United States Patent [19]

Hu et al.

[11] Patent Number: 4,865,870

[45] Date of Patent: Sep. 12, 1989

[54] METHOD FOR RENDERING A SUBSTRATE SURFACE ANTITHROMBOGENIC

[75] Inventors: Can B. Hu; Donald D. Solomon, both of Spring Valley; Nancy L. Shields, Dayton, all of Ohio

[73] Assignee: Becton, Dickinson and Company, Franklin Lakes, N.J.

[21] Appl. No.: 215,974

[22] Filed: Jul. 7, 1988

[51] Int. Cl.[4] .............................................. A01N 1/02
[52] U.S. Cl. ...................................... 427/2; 427/322; 523/112; 525/54.1; 525/54.2; 525/54.22
[58] Field of Search ............... 427/2, 322; 523/112; 525/54.1, 54.2, 54.22

[56] References Cited

U.S. PATENT DOCUMENTS

| | | | |
|---|---|---|---|
| 3,617,344 | 11/1971 | Leeininger et al. | 117/47 |
| 3,634,123 | 1/1972 | Eriksson et al. | 117/47 A |
| 3,810,781 | 5/1974 | Eriksson et al. | 117/47 A |
| 4,118,485 | 10/1978 | Eriksson et al. | 536/1 X |
| 4,349,467 | 9/1982 | Williams et al. | 525/54.2 |
| 4,521,564 | 6/1985 | Solomon et al. | 525/54.1 |
| 4,613,517 | 9/1986 | Williams et al. | 427/2 |

OTHER PUBLICATIONS

Lelah, Michael D. et al, *A Canine Ex Vivo Series Shunt for Evaluating Thrombus Deposition on Polymer Surfaces*, pp. 475–496, 1984.

Primary Examiner—Michael Lusignan
Attorney, Agent, or Firm—Richard E. Brown

[57] ABSTRACT

A method for heparinizing a substrate includes applying a coating of ammonium salt to a substrate by steeping the substrate in a solution of the salt at an alkaline pH and contacting the coated substrate with a solution of a salt of heparin.

21 Claims, 1 Drawing Sheet

METHOD FOR RENDERING A SUBSTRATE SURFACE ANTITHROMBOGENIC

BACKGROUND OF THE INVENTION

1. Field of the Invention

This invention relates to biomedical devices, and more specifically relates to a method for coating a substrate with an antithrombogenic agent.

2. Background of the Invention

Extensive investigations have been undertaken over many years to find materials that will be biologically and chemically stable toward body fluids. This area of research has become increasingly important with the development of various objects and articles which can be in contact with blood, such as artificial organs, vascular grafts, probes, cannulas, catheters and the like.

Synthetic plastics have come to the fore as preferred materials for such articles. However, these materials have the major drawback of being thrombogenic. Thrombogenicity has conventionally been counteracted by the use of anticoagulants such as heparin. Various procedures for attachment of heparin to otherwise thrombogenic polymeric surfaces have been disclosed.

U.S. Pat. No. 4,521,564 to Solomon et al. discloses coating a polymeric article with an amine rich surface and covalently conjugating aldehyde actuated heparin to the amino groups thereof. Leininger et al., in U.S. Pat. No. 3,617,344 discloses a method in which a polymeric surface is chemically modified to include a chloromethyl group. Amination of the chloromethyl group provides a quarternary ammonium halide. Reaction of the halide with sodium heparin results in ionic bonding of the heparin to the surface.

A related approach has been described by Eriksson et al. in U.S. Pat. No. 3,634,123. An article having a plastic surface is heated to near or above its softening point in an aqueous solution of a cationic surface active agent, such as a long chain alkylamine or alkylenediamine hydrohalide. The solution is preacidified to a pH of 7.0 or lower. Subsequent digestion of the plastic article with an aqueous solution of heparin results in an article having about 0.1 International Unit of heparin thereon.

A further improvement is described in U.S. Pat. No. 3,810,781 to Eriksson et al., wherein heparinized plastic surfaces are stabilized with glutaraldehyde.

Williams et al., in U.S. Pat. Nos. 4,349,467 and 4,613,517 discloses modifications of the surface active agent heparin method. The former patent discloses that higher quantities of heparin are attached to a plastic surface by using more concentrated solutions of heparin. The latter patent discloses treating a polymeric surface with a plasma, digesting the plasma treated surface with a quaternary ammonium salt, reacting the salt with sodium heparin, and crosslinking the heparin with glutaraldehyde.

While significant advances have been made toward antithrombogenic surfaces for fabrication of medical devices, further improvements are needed. In particular, materials having surfaces that are essentially non thrombogenic for use in devices which will be in contact with blood for prolonged periods are needed. It is toward fulfillment of this need that this invention is directed.

SUMMARY OF THE INVENTION

A method for heparinizing a substrate includes adjusting the pH of a solution of a surface active agent (SAA) in a solvent to above 7.5, steeping the substrate in the solution of adjusted pH for a time sufficient to coat the SAA onto the substrate, and immersing the coated substrate in a solution of an antithrombogenic agent.

A preferred SAA ia an ammonium salt such as a salt of a primary, secondary or tertiary amine or a quaternary salt. Preferred ammonium salts are soluble in an aqueous medium and have at least one alkyl group of about 8 to 20 carbon atoms. The most preferred salts are salts of secondary amines additionally having at least one alkyl group of about 1 to 4 carbon atoms. A particularly preferred salt is dodecylmethylammonium chloride, hereinafter referred to as DMAC. Preferred antithrombogenic agents are sulfonated polysaccharides, such as dextran sulfate, most preferably heparin.

The pH of the steeping solution may be adjusted to the desired pH by adding an alkalinizing agent such as an amine soluble in the solvent, or, preferably by adding an alkali metal hydroxide.

An optional heparin stabilizing step may be performed by treating the heparinized substrate with a solution of a dialdehyde, such as glutaraldehyde.

In accordance with the invention in which steeping of a substrate with an SAA is carried out at an alkaline pH, the quantity and permanency of heparin which may be bonded to the substrate will be substantially increased compared to prior art heparinization procedures carried out at neutral or acidic pH. In addition, the activity of the heparin bonded by the method of the invention, as determined by platelet deposition, is also substantially improved compared to the prior art procedures. The method of the invention is operationally simpler than the prior art in being carried out at a lower temperature and for a shorter time. With this invention, only low concentrations of ammonium salt are required to affix the heparin thereby reducing the cost of medical articles heparinized by the method of the invention.

DETAILED DESCRIPTION

Figure 1:
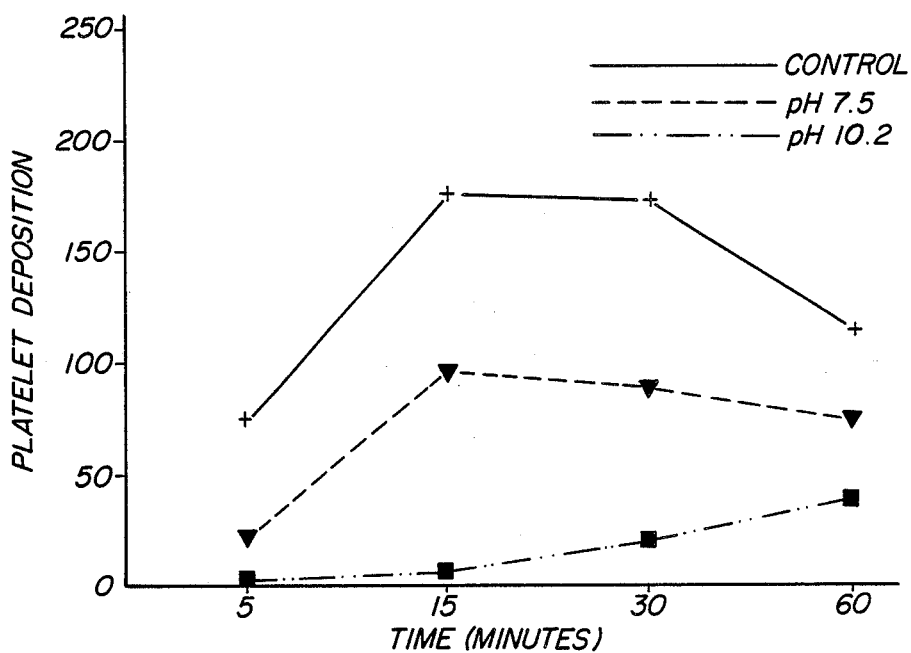
FIG. 1 illustrates platelet deposition on an unheparinized substrate and substrates heparinized by the method of the invention and by a prior art method.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The heparinization method of the invention may be performed on any substrate to be fabricated into an article intended to come into contact with blood. Suitable substrates may be metal, glass or ceramic, with or without a coating of polymer. The invention will hereinafter be described in terms of the preferred substrate, i.e., a polymeric substrate.

The polymeric substrate may be either natural or synthetic, and may be rigid or flexible and porous or nonporous. It may be first formed into any desired shape, size or configuration. Representative of such are valves, pins, containers, sleeves, connectors, medical surgical tubing, prosthetic devices, catheters and the like. Alternatively, the polymeric resin may be first treated by the method of this invention and subsequently fabricated into the desired shape.

Any polymeric resin conventionally used to fabricate articles commonly used in contact with blood may serve as the substrate of the invention. For example, catheters, artificial blood vessels, valves and like prosthetics are frequently fabricated from polyolefins, polyacrylics, polyvinyl chloride, polyamides, polyurethanes, polyurethaneureas, silicone urethane copolymers, polyvinylpyrrolidone, polyvinyl alcohols, cellulose acetate, polystyrene, polyesters, fluorinated polymers, silicone rubber, natural rubber, polycarbonates and like polymeric resins and hydrogels thereof. Preferred substrates are polyurethanes, most preferably polyurethanes having a hardness of from about Shore 45A to Shore 75D.

An ammonium salt of a primary, secondary or tertiary amine, alkylenediamine, or a quarternary ammonium salt or mixture thereof of general formula I may be contacted with the surface of the substrate.

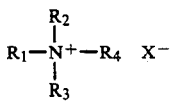   I

In formula I $R_1$ may be an alkyl group, straight chain or branched, of from 1 to 18 carbon atoms, or an aralkyl group of about 7 to 18 carbon atoms, $R_2$, $R_3$ and $R_4$ may independently be hydrogen or $R_1$, and X may be a negative monovalent ion, such as a halide ion. For example, the commercially available quarternary salt benzalkonium chloride wherein $R_1$ is $C_8H_{17}$, $R_2$ is $C_6H_5CH_2$ and $R_3$ and $R_4$ are methyl may be used. Preferred salts are secondary amines wherein $R_3$ and $R_4$ are hydrogen. The most preferred salt is DMAC wherein $R_1$ is dodecyl, $R_2$ is methyl and $R_3$ and $R_4$ are hydrogen.

The surface of the polymeric substrate may be coated with the SAA by steeping the substrate in a dispersion of the salt at the adjusted pH, as described below. The term dispersion is herein meant to include suspension and solution. In the steeping process, it is believed, although not substantiated, that the SAA permeates throughout the molecular structure of the substrate by chemisorption, whereby one or more of the long chain alkyl portions or the salt is effectively bound to the polymeric substrate.

Steeping may be carried out conventionally by immersing the substrate in a solvent or mixture of solvents containing the dispersed salt at the adjusted pH. Any solvent may be used in which the SAA is at least partially dissolved at the adjusted pH of the steeping medium. Suitable solvents are generally polar solvents such as water, alcohols or aqueous alcohols. In some cases, it may be advantageous to add an emulsifying agent to the steeping medium in order to maintain better contact between the substrate and the surface active agent at the adjusted pH.

In the steeping operation, the concentration of compounds I and II in the solvent is not critical, but is advantageously maintained within the range of 0.01% to 20%, preferably 0.1% to 15%, most preferably 0.5% to 50% by weight. (As used herein, all percent ages are by weight unless otherwise indicated.) Steeping may be carried out at a temperature from about 0° C., preferably ambient, up to or slightly above the softening point temperature for the resin substrate. By the term "softening point temperature" is meant the temperature at which the surface of the resin substrate becomes pliable due to the additional mobility of the substrate molecules. The time of steeping is also not critical, and may be from about 1 minute to 24 hours, preferably from about 10 minutes to 2 hours.

Upon completion of the steeping step, the substrate may be removed from the steeping medium and excess SAA may be removed by simple rinsing with a suitable solvent, such as distilled water or saline.

The polymeric substrate bearing the affixed SAA may then be treated with an antithrombogenic agent. Preferred antithrombogenic agents are sulfonated polysaccharides, such as dextran sulfate, or preferably heparin. Heparinization may conveniently be carried out by immersing the substrate bearing the affixed SAA on its surface in a solvent, preferably water. Preferred heparin salts are alkali metal salts, such as sodium heparin. The temperature at which the immersion may advantageously be carried out is from about room temperature to about 80° C., but less than the softening point for the substrate. The time of immersion is dependent on the temperature used, and generally is 8 hours or less. Preferred ranges for the immersion in sodium heparin solution are 30°–50° C. and 10 minutes to 2 hours. The concentration of heparin in the immersing solution is not critical, and may be from about 1 to 15%, preferably about 5–10%.

Following the heparinization step, the substrate is removed from the heparin solution and rinsed thoroughly with distilled water.

In some cases, it may be advantageous to stabilize the heparin toward desorption from the substrate in the presence of blood by treatment with dialdehydes to crosslink functional groups of heparin. This crosslinking of functional groups in different heparin units is accomplished when the heparinized surface is digested with aqueous solutions of a dialdehyde over a concentration range of 0.1% to 5.0%. It is most advantageous to maintain contact between the heparinized surface and the dialdehyde solution for a time period of about 10 minutes to 6 hours at a temperature of ambient to about 80° C. Preferred stabilization conditions are treatment with glutaraldehyde at about 0.5% concentration for about 1 hour at a temperature of about ambient to 45° C. The heparinized surface thus stabilized is removed from the bath, washed thoroughly with distilled water and dried before being brought into contact with blood.

In accordance with the invention, it has surprisingly been found that the quantity and permanency of the bonding of heparin may be greatly increased if the steeping medium is adjusted to an alkaline pH during affixation of the SAA to the substrate.

Aqueous solutions of the salts of the invention and the prior art have pHs in the range of 6.7 to 7.5 depending on the chemical composition of the salt, its concentration in the steeping solvent, and the temperature of the pH measurement. When the steeping step of the invention is carried out with no pH adjustment, minimal quantities of heparin become affixed to the substrate surface, as shown in the Chart below. When the pH is adjusted to the range of 7.5 to 14.0 by the addition of an alkalinizing agent, much greater quantities of heparin may be affixed to the substrate. Suitable alkalinizing agents are soluble amines, as for example, triethylamine, ammonium hydroxide, or, preferably, an alkali metal hydroxide.

The effect of performing steeping at an alkaline pH may be determined by comparing the results obtained under four arbitrarily selected experimental protocols at the acidic and neutral pHs of the prior art with the alkaline pH of the invention. In protocol A, steeping may be carried out for 60 minutes at 45° C., and in protocol B, for 30 minutes at 25° C., both with glutaraldehyde stabilization. Protocols A' and B' are the same as A and B except glutaraldehyde stabilization is not included.

Charts I and II below set forth the quantity in ug/cm², of heparin bonded to a proprietary polyinurethane (PU-P) of Shore hardness 50D and to a commercial polyurethane (PU C, Tecoflex TM) of Shore hardness 80A, with and without glutaraldehyde stabilization, respectively. The initial quantity of bonded heparin and the quantity remaining after 1,2,3 and 5 days of dynamic leaching are given as a measure of the permanency of the bonding by the method of the invention.

CHART I

| Substrate | DMAC Steeping pH | Conc. wt % | Protocol | Bonded Heparin, ug/cm², Remaining After Dynamic Leaching, hours 0 | 24 | 8 | 72 | 120 |
|---|---|---|---|---|---|---|---|---|
| PU-P | 4.3 | 15 | A | .9 | .3 | .3 | 0 | 0 |
| PU-P | 7.5 | 15 | A | 2.2 | .5 | .4 | .1 | .2 |
| PU-P | 8.4 | 15 | A | 6.2 | 2.0 | 1.4 | 1.0 | 1.1 |
| PU-P | 10.2 | 15 | A | 24.7 | 9.1 | 7.4 | 6.0 | 5.2 |
| PU-P | 4.3 | 0.94 | A | 1.0 | 0.7 | 0.7 | 0.3 | 0 |
| PU-P | 7.5 | 0.94 | A | 5.0 | 1.0 | 0.9 | 0.3 | 0.2 |
| PU-P | 8.4 | 0.94 | A | 8.5 | 4.3 | 3.4 | 2.8 | 1.6 |
| PU-P | 10.2 | 0.94 | A | 39.2 | 8.2 | 7.9 | 5.8 | 6.0 |
| PU-P | 7.5 | 0.94 | B | 2.2 | 1.0 | 0.9 | 0.9 | 0.9 |
| PU-P | 10.2 | 0.94 | B | 13.6 | 6.4 | 5.0 | 4.4 | 4.0 |
| PU-P | 13.0 | 0.94 | B | 13.9 | 5.4 | 4.6 | 4.0 | 3.4 |
| PU-P | 7.5 | 2.5 | B | 1.0 | 0.3 | | | |
| PU-P | 10.2 | 2.5 | B | 9.0 | 4.0 | | | |
| PU-P | 7.5 | 5.0 | B | 1.0 | 0.3 | | | |
| PU-P | 10.2 | 5.0 | B | 8.5 | 4.0 | | | |
| PU-P | 4.3 | 15 | B | 2.4 | 0.4 | 0.1 | 0.1 | 0.1 |
| PU-P | 7.5 | 15 | B | 1.1 | 0.5 | 0.1 | 0.1 | 0.1 |
| PU-P | 8.4 | 15 | B | 5.2 | 0.8 | 0.3 | 0.4 | 0.3 |
| PU-P | 10.2 | 15 | B | 7.0 | 1.8 | 1.2 | 1.1 | 1.1 |
| PU-C | 4.3 | 0.94 | B | 1.6 | 0.4 | | | |
| PU-C | 7.5 | 0.94 | B | 5.0 | 2.2 | | | |
| PU-C | 8.4 | 0.94 | B | 17.6 | 7.5 | | | |
| PU-C | 10.2 | 0.94 | B | 39.4 | 13.3 | | | |
| PU-C | 7.5 | 2.5 | B | 2.2 | 1.1 | | | |
| PU-C | 10.2 | 2.5 | B | 28.0 | 17.0 | | | |
| PU-C | 7.5 | 5.0 | B | 1.6 | 1.0 | | | |
| PU-C | 10.2 | 5.0 | B | 37.0 | 17.0 | | | |

CHART I

| Substrate | DMAC Steeping pH | Conc. wt % | Protocol | Bonded Heparin, ug/cm² remaining After dynamic leaching, hours 0 | 24 | 8 | 72 | 120 |
|---|---|---|---|---|---|---|---|---|
| PU-P | 4.3 | 15 | A' | 2.3 | 0.3 | 0.3 | 0 | 0 |
| PU-P | 7.5 | 15 | A' | 2.5 | 0.5 | 0.4 | 0 | 0 |
| PU-P | 8.4 | 15 | A' | 8.4 | 2.1 | 1.4 | 0.8 | 0.9 |
| PU-P | 10.2 | 15 | A' | 25 | 6.3 | 4.2 | 3.0 | 3.5 |
| PU-P | 4.3 | 0.94 | A' | 1.2 | 0.6 | 0.6 | 0 | 0 |
| PU-P | 7.5 | 0.94 | A' | 6.0 | 0.9 | 0.8 | 0.2 | 0.2 |
| PU-P | 8.4 | 0.94 | A' | 13.9 | 2.0 | 1.7 | 0.9 | 0.9 |
| PU-P | 10.2 | 0.94 | A' | 27.1 | 4.2 | 3.1 | 2.1 | 2.2 |
| PU-P | 7.5 | 0.94 | B' | 2.4 | 1.2 | 1.0 | 1.0 | 0.9 |
| PU-P | 10.2 | 0.94 | B' | 18.4 | 9.9 | 7.2 | 6.4 | 4.9 |
| PU-P | 13 | 0.94 | B' | 16.4 | 8.4 | 6.2 | 5.9 | 4.6 |
| PU-P | 4.3 | 15 | B' | 1.5 | 0.4 | 0.1 | 0.2 | 0.1 |
| PU-P | 7.5 | 15 | B' | 2.5 | 0.6 | 0.1 | 0.3 | 0.2 |
| PU-P | 8.4 | 15 | B' | 2.9 | 0.7 | 0.4 | 0.4 | 0.3 |

CHART I-continued

| Substrate | DMAC Steeping pH | Conc. wt % | Protocol | Bonded Heparin, ug/cm² remaining After dynamic leaching, hours 0 | 24 | 8 | 72 | 120 |
|---|---|---|---|---|---|---|---|---|
| PU-P | 10.2 | 15 | B' | 7.1 | 2.0 | 1.2 | 1.3 | 1.1 |
| PU-C | 4.3 | 0.94 | B' | 2.0 | 0.6 | | | |
| PU-C | 7.5 | 0.94 | B' | 7.3 | 2.3 | | | |
| PU-C | 8.4 | 0.94 | B' | 26.2 | 8.5 | | | |
| PU-C | 10.2 | 0.94 | B' | 51.4 | 20.2 | | | |

It is readily seen from the Charts that, regardless of the substrate, time, temperature or concentration of the preferred DMAC during steeping, the quantity and permanency of heparin bonded to the substrate is increased by up to 1100% at a pH of 10.2 relative to a prior art pH of 7.5. Further, it is seen that, although a significant portion of the bonded heparin is washed off the substrate over a period of 5 days, in all cases, a much greater quantity of heparin remains on the substrate after a 5 day dynamic leaching in accordance with Example II when the steeping is carried out at a pH of about 10.2 rather than 7.5.

The effect of the optional glutaraldehyde stabilization of heparin bonded by the method of the invention may be determined by comparing, in Charts I and II, quantities of heparin on the substrate with and without glutaraldehyde treatment. In general, it is found that anywhere from about 0 to 100% more heparin remains on the PU-P substrate of higher hardness after prolonged leaching when glutaraldehyde is used. Surprisingly, however, glutaraldehyde treatment does not improve the permanency of bonded heparin on the softer Tecoflex TM substrate.

Figure 2:
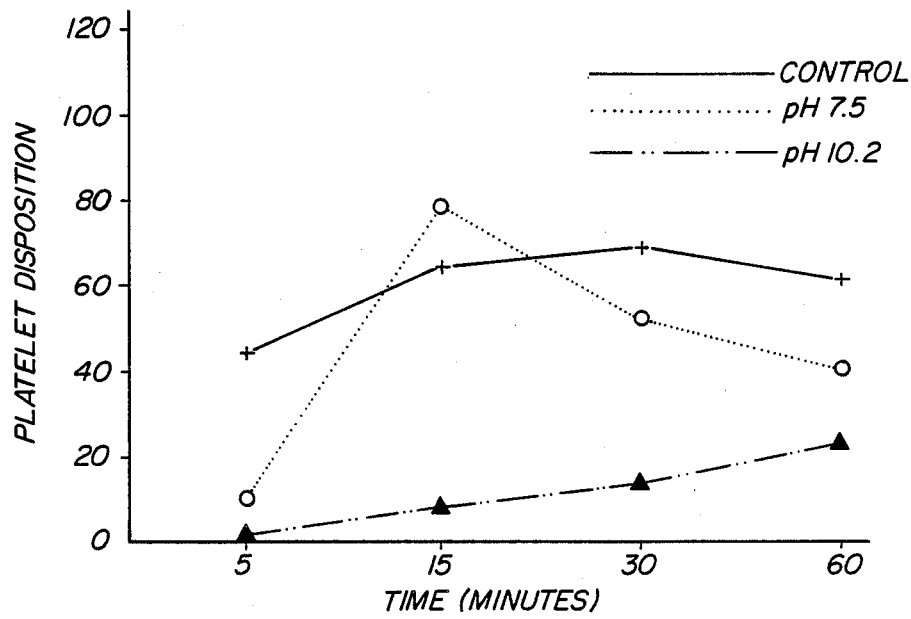
FIG. 2 illustrates platelet deposition on the substrates of FIG. 1 after washing with normal saline.

The activity of the heparin bonded by the method of the invention may be determined with an ex vivo shunt model, as described by Lelah et al, in *Journal of Biomedical Materials Research* 18, 475 (1984). In this procedure, platelet deposition on a surface as a function of time is measured. FIG. 1 compares platelet deposition on a control (unheparinized) 3 mm PU-P tubing and on the same tubing heparinized in accordance with Example IV. FIG. 2 compares platelet deposition on the same substrates after washing with normal saline. It is seen that at each of the 5,15,30 and 60 minute times studied, with and without saline wash, the substrate heparinized according to the invention has substantially less deposited platelets than the control substrate or the substrate heparinized with steeping at pH 7.5 in accordance with the prior art. In another embodiment of the method of the invention, the substrate may be treated with a plasma in accordance with the procedure of Williams et al. prior to the steeping step. This optional plasma treatment, while not essential to the method of the invention, may be advantageous in preparation of id, hydrophobic surfaces such as polypropylene and polytetrafluoroethylene for steeping and heparinization to the method of the invention. The following examples are provided to further describe the invention but are in no way to be considered as limitative of the invention.

EXPERIMENTAL Solutions used in the following examples were prepared as follows:

1. 15% DMAC Stock Solution:

Distilled water, 800 ml., was preheated to 45° C. and 145 g. of DMAC was then dissolved completely therein. The pH of the final DMAC solution was adjusted either with 1N hydrochloric acid or 5N sodium hydroxide solution to the desired pH. The solution was then adjusted with distilled water to a final volume of 967 ml.

2. 5.0, 2.5, and 0.94% DMAC Solutions:

These solutions were prepared by appropriate dilutions of the 15% DMAC stock solution. The pHs of the solutions were monitored again after the dilutions and readjusted to the desired value, if necessary.

3. 9% $^3$H-Heparin Solution:

33.75 grams of sodium heparin and 500 uCi tritium labelled heparin were dissolved in 375 mls distilled water at room temperature with good agitation. The final concentration of heparin was 9% and the tritium activity was 1.33 uCi/ml.

4. 0.5% Glutaraldehyde Solution:

This solution was prepared either by diluting 1 ml of 50% glutaraldehyde solution with 99 mls of distilled water or by diluting 2 mls of 25% glutaraldehyde solution with 98 mls of distilled water.

EXAMPLE I

General Procedures for Heparinization The polymeric substrate was steeped for a preselected time at a preselected temperature in an aqueous solution of DMAC of preselected concentration at a pH of 4.3, 7.5, 8.4, 10.2 and 13.0. The substrate was removed from the steeping solution and immersed in a 9% aqueous solution of sodium heparin for either 60 minutes at 45° C. or 30 minutes at 25° C. The heparinized substrates were removed from the immersing solution, rinsed to remove excess heparin solution and optionally stabilized by immersing in a 0.5% aqueous solution of glutaraldehyde for 1 hour at the same temperature as used for steeping. The permanency of the heparin attachment was determined by the leach rate study of Example II. The quantity of heparin bonded was determined by the procedure of Example III.

EXAMPLE II

Leach Rate Study for Determination of Permanency of Bonded Heparin

Coated samples were dynamically leached in 1 l of normal saline (NS) using a stir plate at ambient temperature for up to 5 days. Saline solution was changed daily. Samples were removed every 24 hours and tested for quantity of heparin remaining by the procedure of Example III.

EXAMPLE III

Determination of Quantity of Bonded Heparin

The DMAC coated substrate was heparinized in accordance with Example I using a mixture of predetermined quantities of heparin and tritiated heparin. The tube, after the optional glutaraldehyde stabilization, was dissolved in tetrahydrofuran, Insta gel ™ scintillation cocktail was added, and the DPM (disintegrated counts per minute) was determined. The DPM was compared with a standard curve prepared from solutions containing known quantities of tritiated heparin.

EXAMPLE IV

Determination of Activity of Bonded Heparin

Sections of PU-P tubing 5 cm long were heparinized by the procedure of Example I using protocol B, a 0.94% aqueous solution of DMAC, and a pH of 7.5 and 10.2. Platelet deposition studies on these heparinized tubings and a control tubing were performed according to the ex vivo shunt model of Lelah et al., supra. The average number of deposited platelets in three dogs is illustrated in FIG. 1. It is seen that the number of deposited platelets was significantly less for tubing heparinized at pH 10.2 than for control tubing and tubing heparinized at pH 7.5.

EXAMPLE V

Determination of Activity of Bonded

Heparin After Normal Saline Wash The heparinized PU-P tubings from Example IV were washed with 8000 ml of normal saline at a rate of 50 ml/min followed by 1000 ml of distilled water at a rate of 150 ml/min. These tubings and control tubing were evaluated for platelet deposition by the ex vivo shunt model. FIG. 2 shows that, even after normal saline wash, the number of deposited platelets was significantly less for tubings heparinized at pH 10.2 than for tubings heparinized at pH 7.5 or control tubing.

What is claimed is:

1. A method for heparinizing a polymeric substrate comprising:
    (a) adjusting the pH of a solution of a surface active agent of the ammonium salt type in a solvent to above 7.5, said surface active agent having at least one alkyl group of 8 to 20 carbon atoms;
    (b) steeping a polymeric substrate in said solution of adjusted pH whereby a coating of said surface active agent forms on said substrate;
    (c removing said substrate having said coating from said solution of adjusted pH; and
    (d) immersing said substrate having said coating in a solution of heparin whereby said heparin reacts with said coating of surface active agent to give a heparinized substrate.

2. The method of claim 1 wherein said polymeric substrate is selected from the group consisting of polyolefin, polyvinyl, polyacrylic, polyester, polyamide, polycarbonate, fluorinated polymer, cellulose acetate, silicone rubber and natural rubber, polyurethane, polyurethaneurea and silicone urethane copolymer.

3. The method of claim 1 wherein surface active agent is selected from the group consisting of a salt of a primary amine, secondary amine, tertiary amine, alkylenediame and a quaternary salt.

4. The method of claim 3 wherein said surface active agent is a secondary amine salt having at least one alkyl group of about 1 to 4 carbon atoms.

5. The method of claim 4 wherein said salt is dodecylmethylamine hydrochloride.

6. The method of claim 1 wherein said pH after adjusting is between from about 8 and 14.

7. The method of claim 1 wherein said adjusting is performed by adding an alkalinizing agent.

8. The method of claim 6 wherein said alkalinizing agent is selected from the group consisting of an amine soluble in said solvent, a metal hydroxide and ammonium hydroxide.

9. The method of claim 7 wherein said alkalinizing agent is an alkali metal hydroxide.

10. The method of claim 1 further comprising treating said heparinized substrate with a dialdehyde to stabilize said heparin.

11. The method of claim 10 wherein said dialdehyde is glutaraldehyde.

12. The method of claim 1 further comprising treating said polymeric substrate with a plasma prior to immersing said substrate in said solution of ammonium salt.

13. The method of claim 12 wherein said polymeric substrate is selected from the group consisting of polypropylene and polytetrafluoro ethylene 14. A method for rendering a substrate antithrombogenic comprising:
   (a) adjusting the pH of a dispersion of a surface active agent of the ammonium salt type in a solvent to above 7.5;
   (b) steeping a substrate in said solution of adjusted pH thereby causing a coating of said surface active agent to form on said substrate;
   (c) removing said substrate having said coating thereon from said solution of adjusted pH; and
   (d) immersing said substrate having said coating thereon in a solution of a sulfonated polysaccharide whereby said polysaccharide reacts with said coating of surface active agent to give an antithrombogenic substrate.

15. The method of claim 14 wherein said substrate may be of a material selected from the group consisting of metal, glass, ceramic and polymer.

16. A method for heparinizing a polymeric substrate comprising:
   (a) adjusting the pH of a solution of dodecylmethylammonium chloride in aqueous medium by adding a sufficient quantity of an alkalinizing agent to raise the pH of said solution to about 10.2;
   (b) steeping a polymeric substrate in said solution of pH about 10.2 whereby a coating of dodecylmethylamine forms on said substrate;
   (c) removing said substrate having said coating from said solution of pH about 10.2; and
   (d) immersing said substrate having said coating in a solution of heparin, said heparin reacting with said coating to give a heparinized substrate.

17. The method of claim 16 wherein said alkalinizing agent is selected from the group consisting of a water soluble amine, ammonium hydroxide and an alkali metal hydroxide.

18. The method of claim 16 wherein said substrate is polyurethane.

19. The method of claim 16 further comprising treating said heparinized surface with glutaraldehyde to stabilize said heparin.

20. The method of claim 16 wherein said substrate is selected from the group consisting of polypropylene and polytetrafluoroethylene.

21. The method of claim 20 further comprising treating said substrate with a plasma prior to immersing said substrate in said solution of dodecyl methyl ammonium chloride.

* * * * *